(12) United States Patent
Barth et al.

(10) Patent No.: US 10,165,998 B2
(45) Date of Patent: Jan. 1, 2019

(54) METHOD AND SYSTEM FOR DETERMINING AN ANGLE BETWEEN TWO PARTS OF A BONE

(71) Applicant: SIEMENS AKTIENGESELLSCHAFT, Munich (DE)

(72) Inventors: Karl Barth, Hoechstadt (DE); Alexander Gemmel, Erlangen (DE); Gerhard Kleinszig, Forchheim (DE); Wei Wei, Erlangen (DE); Markus Weiten, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 295 days.

(21) Appl. No.: 15/003,876

(22) Filed: Jan. 22, 2016

(65) Prior Publication Data

US 2016/0213343 A1 Jul. 28, 2016

(30) Foreign Application Priority Data

Jan. 22, 2015 (DE) .......................... 10 2015 201 067

(51) Int. Cl.
*A61B 6/00* (2006.01)
*A61B 5/107* (2006.01)
(Continued)

(52) U.S. Cl.
CPC ............ *A61B 6/505* (2013.01); *A61B 5/1071* (2013.01); *A61B 5/4504* (2013.01); *A61B 6/12* (2013.01); *A61B 6/4441* (2013.01); *A61B 6/5217* (2013.01)

(58) Field of Classification Search
CPC ....... A61B 5/1071; A61B 5/4504; A61B 6/12; A61B 6/505; A61B 6/5217
See application file for complete search history.

(56) References Cited

U.S. PATENT DOCUMENTS 5,623,528 A * 4/1997 Takeda ................ A61B 6/4216
250/582
5,728,128 A * 3/1998 Crickenberger ...... A61F 2/4657
606/102

(Continued)

FOREIGN PATENT DOCUMENTS

DE 212012000054 U1 11/2013
EP 2801320 A1 11/2014
(Continued)

OTHER PUBLICATIONS

Wolf, H., et al., "Rotationsfehler nach Marknagelung des Oberschenkels", Unfallchirurgie, vol. 10, 1984, pp. 133-136, No. 3—English abstract.

(Continued)

*Primary Examiner* — Glen Kao
(74) *Attorney, Agent, or Firm* — Laurence Greenberg; Werner Stemer; Ralph Locher

(57) ABSTRACT

A method and a system for determining an angle between two parts of a bone that are twisted relative to one another about the axis of a bone shaft. The system is particularly suitable for determining the antetorsion angle of a femur. In order to determine an antetorsion angle of a bone easily intraoperatively, a method with the following steps is proposed: establishing the position of a first orientation feature assigned to a first part of the bone, in particular a femoral neck axis, using an imaging method, establishing the position of a second orientation feature assigned to a second part of the bone, in particular a condyle tangent or a condyle plane, using an imaging method, and determining the angle, in particular the femoral antetorsion angle, from the positions of the two orientation features.

12 Claims, 2 Drawing Sheets

(51) Int. Cl.
  *A61B 5/00* (2006.01)
  *A61B 6/12* (2006.01)

(56) References Cited

U.S. PATENT DOCUMENTS

| | | |
|---|---|---|
| 8,064,660 B2 | 11/2011 | Leow et al. |
| 2007/0161929 A1 | 7/2007 | Maier |
| 2012/0213329 A1* | 8/2012 | Holum, Jr. ............... A61B 6/14 378/38 |
| 2013/0129044 A1 | 5/2013 | Yoon et al. |
| 2013/0317512 A1 | 11/2013 | Bühren et al. |
| 2013/0322726 A1 | 12/2013 | Nathaniel |
| 2015/0265361 A1 | 9/2015 | Blau et al. |

FOREIGN PATENT DOCUMENTS

| | | |
|---|---|---|
| EP | 2801321 A2 | 11/2014 |
| WO | 2005083635 A1 | 9/2005 |
| WO | 2014048447 A1 | 4/2014 |

OTHER PUBLICATIONS

Strecker, W., et al., "Computertomographische Torsionswinkelbestimmung der unteren Extremitaeten", Unfallchirurgie, vol. 97, 1994, pp. 609-613—English abstract.

* cited by examiner

METHOD AND SYSTEM FOR DETERMINING AN ANGLE BETWEEN TWO PARTS OF A BONE

CROSS-REFERENCE TO RELATED APPLICATION

This application claims the priority, under 35 U.S.C. § 119, of German patent application DE 10 2015 201 067.8, filed Jan. 22, 2015; the prior application is herewith incorporated by reference in its entirety.

BACKGROUND OF THE INVENTION

Field of the Invention

The invention relates to a method and a system for determining an angle between two parts of a bone that are twisted relative to one another about the axis of a bone shaft. The method and system are particularly suited for determining the antetorsion angle of a femur.

When fractures are treated by surgery, great importance is placed on the alignment of the fragments, created by the break, in relation to one another. Here, the fragments must be positioned anatomically correctly. This is particularly important in the case of bones, the incorrect growing together of which may lead to postural disorders, movement restrictions or overloading of joint structures of the patient, such as, for example, at the femur.

The position of the proximal and distal joint-forming structures of the femur, twisted relative to one another along the femoral shaft axis, is usually specified by the femoral antetorsion angle. In the case of a fracture of the femoral shaft, this position twisted in relation to one another, i.e. the correct antetorsion angle, must be reestablished. Leg malalignments are among the very frequent complications in the case of femoral bone shaft fractures. If the malalignment is too great, i.e. if the antetorsion angles of the two sides deviate too much from one another, the malalignment must be revised and the patient must be operated on again. This applies not only to fractures of the femur, but also to fractures of other bones in which specific angles of the bone fragments are to be set during repositioning.

During the operation, the position of the bone fragments in relation to one another is merely set in most cases on the basis of the mobility thereof and by virtue of an external comparison. Sometimes there is a check by means of an imaging method, such as e.g. 3D computed tomography, postoperatively and generally outside of the operating theater.

United States patent application publication US 2007/0161929 A1 describes a method in which a torsion angle is determined with the aid of analysis software that evaluates the recorded image. The evaluation of x-ray images by means of image analysis is also known from U.S. Pat. No. 8,064,660 B2 and its counterpart international patent application WO 2005/083635 A1; there, it is for the purpose of identifying bone fractures.

United States patent application publications Nos. US 2013/0129044 A1 (EP 2 801 321), US 2015/0265361 A1 (WO 2014/048447 A1) and US 2013/0322726 A1 (DE 21 2012 000 054 U1) describe methods in which the recording device is aligned in relation to the patient, or the position of a bone can be determined, using a visible stationary reference body in the x-ray image.

United States patent application publication US 2013/0317512 A1 likewise describes the use of a reference object. The reference object therein is connected to a bone implant and therefore shows the position of the bone.

In a known method, an attempt is made during the operation to transfer the anatomical conditions of the healthy side to the side with a fracture. By way of example, the so-called trochanter minor method serves to this end; the goal of the latter is to set the antetorsion of the two bones of a femoral pair to be as equal as possible with the aid of x-ray images in the AP direction and therefore to minimize the torsion angle difference intraoperatively. To this end, the contour of the trochanter minor of the fractured femur is compared to the corresponding contour of the healthy bone. To this end, the injured thigh must be introduced into the beam path under identical positioning conditions. Moreover, a precondition for applying this method is that the trochanter minor is undamaged. Moreover, similarities between the trochanter minors can only be visually assessed with difficulty in projection images.

Recently, a method in which the antetorsion is determinable intraoperatively using 3D x-ray imaging was proposed. However, this method is not universally applicable since no x-ray machine suitable for the generation of 3D recordings is available during an operation in most cases.

BRIEF SUMMARY OF THE INVENTION

It is accordingly an object of the invention to provide a method and a system for determining the angle between two portions of a bone which overcome the above-mentioned and other disadvantages of the heretofore-known devices and methods of this general type and which allows the angle between two parts of a bone that are twisted relative to one another about the axis of a bone shaft, in particular an antetorsion angle of a bone, to be determined intraoperatively with simple means.

With the foregoing and other objects in view there is provided, in accordance with the invention, a method of determining an angle between two parts of a bone that are twisted relative to one another about an axis of a bone shaft of the bone. The method comprising:

establishing a position of a first orientation feature assigned to a first part of the bone using an imaging method;

establishing a position of a second orientation feature assigned to a second part of the bone using an imaging method;

for establishing the position of at least one of the first and second orientation features, positioning an indication element relative to the at least one of the first and second orientation feature, and positioning the indication element based on a plurality of recordings obtained by the imaging method; and determining the angle between the first and second parts of the bone from the positions of the first and second orientation features.

In a preferred implementation of the invention, the bone is a femur, the first orientation feature is a femoral neck axis, the second orientation feature is a condyle tangent or a condyle plane, and the determining step comprises determining a femoral antetorsion angle.

In other words, the method according to the invention for determining an angle between two parts of the bone twisted relative to one another about the axis of a bone shaft, in particular for determining the antetorsion angle of a femur, comprises the following steps: establishing the position of a first orientation feature assigned to a first part of the bone, in particular a femoral neck axis, using an imaging method, establishing the position of a second orientation feature assigned to a second part of the bone, in particular a condyle tangent or a condyle plane, using an imaging method, and determining the angle, in particular a femoral antetorsion angle, from the positions of the two orientation features.

According to the invention, an indication element is positioned relative to the relevant orientation feature, in particular parallel to said orientation feature, when establishing the position of at least one of the orientation features, in particular when establishing the position of the femoral neck axis, wherein the positioning is implemented on the basis of a number of recordings obtained by the imaging method.

The system according to the invention for determining an angle between two parts of the bone twisted relative to one another about the axis of a bone shaft, in particular for determining the antetorsion angle of a femur, comprises: means for establishing the position of a first orientation feature assigned to a first part of the bone, in particular a femoral neck axis, means for establishing the position of a second orientation feature assigned to a second part of the bone, in particular a condyle tangent or a condyle plane, and means for determining the angle, in particular a femoral antetorsion angle, from the positions of the two orientation features. According to the invention, the means for establishing the position of the orientation feature assigned to the first part of the bone comprise at least one indication element positionable relative to the relevant orientation feature on the basis of a number of recordings obtained by the imaging method.

A core concept of the invention lies in making the antetorsion angle determinable with the aid of simple 2D x-ray recordings, as can be produced by means of imaging methods with recording devices that are available in many operations. An antetorsion angle of a healthy bone established thus can be used to set the antetorsion angle of a repositioned bone accordingly. In order to establish the antetorsion angle of the repositioned bone, use can likewise be made of the method according to the invention. Overall, the torsion angle error is minimized intraoperatively in a simple manner. This takes place purely with the use of projection recordings, i.e. without a 3D x-ray device needing to be available therefor.

It is advantageous that the injured femur need not be introduced into the beam path under identical positioning conditions. At the same time, the torsion angle can be determined with a comparatively high accuracy of a few degrees of deviation with the aid of the method according to the invention. The reproduction accuracy of the angle determination is likewise comparatively high. Using the invention, the quality of the treatment of bone fractures, in particular of femur bone shaft fractures, is increased and the revision rate due to incorrect torsion angles is significantly reduced.

Moreover, it is advantageous that only bone-inherent orientation features are used. Additional elements, such as e.g. markers, are therefore not required for establishing the position of the bone parts. The whole angle determination is moreover implemented in a non-invasive manner and it is therefore a particularly sparing method which can therefore also be used for determining angles on the healthy side.

It is particularly advantageous if the recordings of the bone used for the positioning of the indication element are recorded from different recording angles. As a result, establishing the position can be completed using a particularly small number of recordings.

In a preferred embodiment of the invention recordings of the bone are made when establishing the position of at least one of the orientation features, in particular when establishing the position of the condyle tangent or the condyle plane, using the imaging method and the recording device is aligned in a desired target position relative to the relevant orientation feature, in particular perpendicular to this orientation feature, on the basis of these recordings.

In a preferred embodiment of the invention, the imaging method used when establishing the position of the first and/or the second orientation feature is an x-ray projection method. Apparatuses for carrying out this comparatively simple method are available in many operating theaters. Thus, no 3D x-ray devices need to be procured to carry out the invention.

The invention can be applied particularly advantageously with mobile and stationary C-arm x-ray devices since, in that case, the geometry, in particular the tube-detector distance, is known and unchangingly constant and the central x-ray beam is always perpendicular to the detector plane. However, the invention can also be performed with other x-ray devices, in particular also with conventional x-ray devices, even if, in that case, it is more difficult to perform the calibration and establish the sought-after angle values.

The invention serves to determine an angle between two parts of a bone twisted relative to one another about the axis of a bone shaft, in particular for determining the antetorsion angle of a fractured femoral bone, and it can preferably be applied in the field of trauma surgery, in particular for repositioning bone fragments.

Other features which are considered as characteristic for the invention are set forth in the appended claims.

Although the invention is illustrated and described herein as embodied in determining an angle between two parts of a bone, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
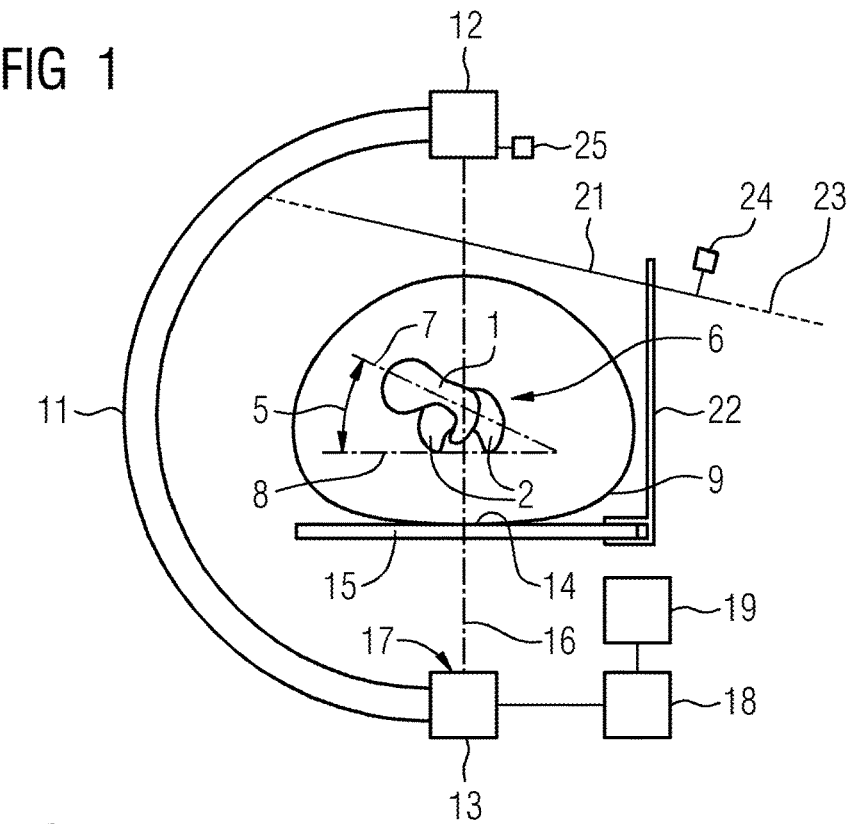
FIG. 1 is a side view of a C-arm device during the implementation of the invention.
Figure 2:
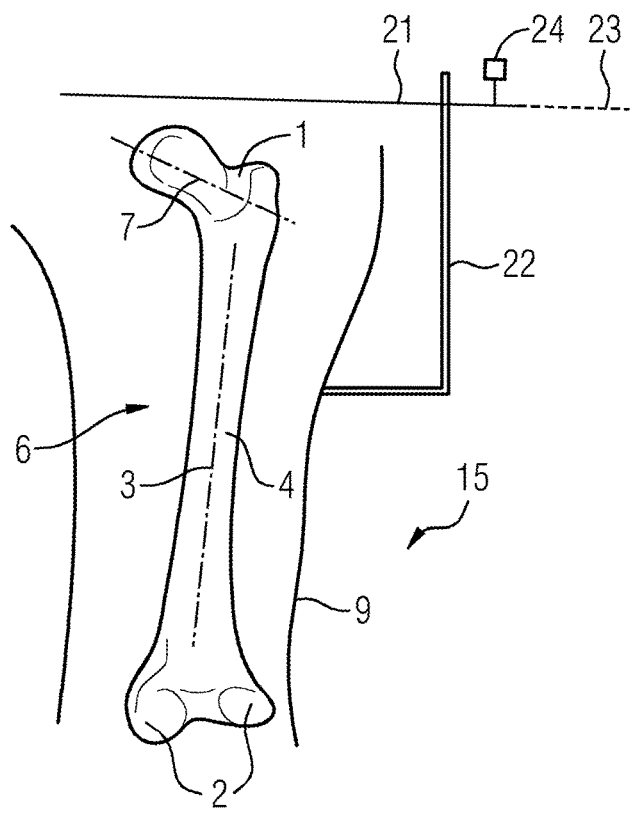
FIG. 2 shows a view from above.

The figures of the drawing show the invention merely highly schematically and only with the primarily important components thereof. The same reference signs correspond to elements with the same or a comparable function throughout.

Referring now to the figures of the drawing in detail the invention will be described using the example of a femoral bone fracture. The system according to the invention is suitable for intraoperative determination of an angle between two parts of a bone that are twisted relative to one another about the axis of a bone shaft. In this case it is for the determination of the angle between the femoral neck 1 and the femoral condyles 2, which are arranged in a manner twisted relative to one another along the femoral shaft axis 3 of the femoral shaft 4, more precisely for determination of the antetorsion angle 5 of the femur 6, i.e. of the angle enclosed between the femoral neck axis 7 and the femoral condyle tangent 8.

The system comprises an imaging device, in this case a 2D x-ray device, in particular a mobile or stationary C-arm x-ray device 11 for producing simple x-ray projection recordings. The method can be implemented not only with a motor-driven C-arm, but also with a simple, manually displaceable C-arm.

The C-arm 11 comprises an x-ray radiation source 12 and an x-ray radiation receiver 13 for producing an x-ray recording of a region, arranged between the x-ray radiation source 12 and the x-ray radiation receiver 13 and acquired by a beam from the x-ray radiation source 12, of the patient body 9 lying in a patient plane 14 on an operating table 15. The C-arm 11 is adjustable by motor in a known manner along the circumference thereof within a certain angle range in order to obtain 2D projections from different projection angles. The x-ray radiation receiver 13 is usually a flat-panel detector. The patient plane 14 lies parallel to the x-ray radiation receiver 13 such that the central x-ray beam 16 is perpendicular to the detector plane 17.

In order to carry out the method according to the invention, the position of a first orientation feature assigned to a first part of the bone is established, in this case the position of the femoral neck axis 7 assigned to the femoral neck 1. To this end, the system includes an indication element 21, or indicator 21. By way of example, a Kirschner wire can be used as indication element 21. However, a different elongate construction element suitable for indicating a direction and preferably having a defined longitudinal axis, for example a rod-shaped or pin-shaped construction element, can be used as indication element 21 as long as it is alignable parallel to the femoral neck axis 7 and visible in the x-ray image to be recorded.

In order to determine the position of the femoral neck axis 7, the indication element 21 is initially positioned parallel to the femoral neck axis 7 using as few x-ray recordings as possible. Subsequently, the position of the femoral neck axis 7 can be identified in space by way of the indication element 21.

The indication element 21 is positioned outside of the patient body 9; in the case of a femoral fracture described here, the indication element 21 is situated above the leg of the patient. Here, the indication element 21 is held manually, for example by a medical practitioner or an assistant, or by means of a suitable mechanical holder 22, for example by means of a frame structure fastenable to the operating table 15 that is adjustable along a plurality of axes, or by means of a stand. In one embodiment of the invention, use is made of a holder provided with a drive. The drive is connected to a suitable control device in such a way that the indication element 21 is positioned automatically or semi-automatically on the basis of an evaluation of the x-ray images.

In order to achieve the desired positioning of the indication element 21 by using or by evaluating as few x-ray recordings as possible, the C-arm 11 is initially brought into an AP position and positioned in the region of the femoral neck 1. In this position, the operating table 15 is oriented perpendicular to the central ray 16 of the C-arm 11. The detector plane 17 of the x-ray radiation receiver 13 of the C-arm 11 thus lies parallel to the patient plane 14, which corresponds to the plane of the operating table 15. At least one x-ray image is recorded in this position. Then the indication element 21 is aligned manually or (semi-)automatically in the detector plane 17 of the C-arm 11 under manual or automatic evaluation of this AP x-ray image in such a way that the longitudinal axis 23 of the indication element 21 is parallel to the femoral neck axis 7 in the available projection recording. In so doing, the indication element 21 is only rotated about an axis perpendicular to the operating table 15, i.e. there is a rotation in the table plane. Optionally, further x-ray images are recorded for verification purposes or for an even more exact alignment of the indication element 21.

The indication element 21 aligned thus indicates the position of the femoral neck axis 7 in the table plane of the operating table 15, but it does not indicate the inclination of the femoral neck axis 7 in relation to the plane of the operating table 15. Therefore, there subsequently is at least one recording of the femur 6 from a recording angle that differs from the previous recording angle of the C-arm 11. To this end, the C-arm 11 is slightly swiveled in an angular and/or orbital manner, for example by 20° to 30°, to be precise preferably in such a way that the central beam 16 thereof is as perpendicular as possible to the indication element 21. The detector plane 17 now lies obliquely in relation to the plane of the operating table 15. Now, at least one x-ray image is recorded anew. Then, the longitudinal axis 23 of the indication element 21 is likewise set parallel to the femoral neck axis 7 in the further projection recording, as was already done in the preceding position of the C-arm 11. Here, all that is changed is the inclination of the indication element 21 in relation to the plane of the operating table 15. Optionally, further x-ray images are once again recorded for verification purposes or for an even more exact alignment of the indication element 21.

Then, the angle position of the indication element 21 corresponds to the rotation angle of the femur neck 1 with great accuracy, respectively in relation to a defined zero position, in this case the plane of the operating table 15 and hence the patient plane 14.

The angle position of the indication element 21 is determined with the aid of a suitable angle measuring device 24 as angle measurement value. By way of example, a gyroscopic sensor is attached to the indication element 21 for the purposes of measuring the angle. Preferably, this sensor is initially calibrated in relation to the angle measurement values of the C-arm 11.

In order to carry out the method according to the invention, the position of a second orientation feature assigned to a second part of the bone, in this case the position of the condyle tangents 8 lying in the femoral condyle plane, is moreover established.

To this end, recordings of the femur 6 are made using the C-arm 11 and the C-arm 11 is aligned into a desired target position relative to the relevant orientation feature, in this case perpendicular to the condyle tangents 8, on the basis of these recordings. In the process, the C-arm 11 is positioned in relation to the femur 6 in such a way that the central ray 16 of the C-arm 11 extends parallel to the condyle tangents 8.

Carrying out the method assumes that the respectively current angle position of the C-arm 11, in particular the position of the central ray 16, is known or establishable. To this end, the angle position of the C-arm 11 relative to a defined zero position, for example relative to the plane of the operating table 15, is establishable as an angle measurement value 26, either from the internal settings of the C-arm 11, for example when using a C-arm with an encoder, or by means of a suitable angle measuring device 25, for example a gyroscopic sensor, attached to the C-arm 11. An initial system calibration may be required to obtain an assignment of an angle position of the C-arm 11 to the x-ray images during the recording of the x-ray images.

In order to determine the position of the condyle tangents 8, the C-arm 11 is initially brought into a lateral position and focused onto the condyles 2. Then, the C-arm 11 is set and positioned on the basis of these lateral x-ray recordings in such a way that the two condyles 2 are depicted in an overlapping manner, preferably in the vicinity of the image center. Additionally, the femoral shaft axis 3 should be as parallel as possible to the horizontal image axis. After completion of the setting of the C-arm 11, the condyle tangent 8 extends perpendicular to the image plane, approximately in the image center. The angle of the condyle tangent 8 in relation to the zero position emerges directly from the angle measurement value 26 of the C-arm 11 in this case.

Subsequently, the femoral antetorsion angle 5 is established from the positions of the two orientation features, in this case from the angle values of the femoral neck axis 7 and the condyle tangent 8. Here, the angle measurement values are not scalar angle values; instead, they specify the directions of the respective axes.

For this purpose, the angle measurement value of the angle measuring device 24 attached to the indication element 21 and the angle measurement value of the angle measuring device 25 attached to the C-arm 11 are made available to an evaluation unit, which, to this end, is connected to the two angle measuring devices 24, 25 or which is connectable thereto, at least from time to time. The evaluation unit can also be the control unit 18 of the C-arm 11.

The antetorsion angle 5 emerges from the angle between the femoral neck axis 7 and the condyle tangent 8. Under the assumption that the angle measuring devices 24, 25 were initially calibrated in relation to one another, the femoral neck axis 7 and the condyle tangent 8 can be transferred into a common coordinate system. Thereupon it is possible to determine the angle between the two axes.

Figure 3:
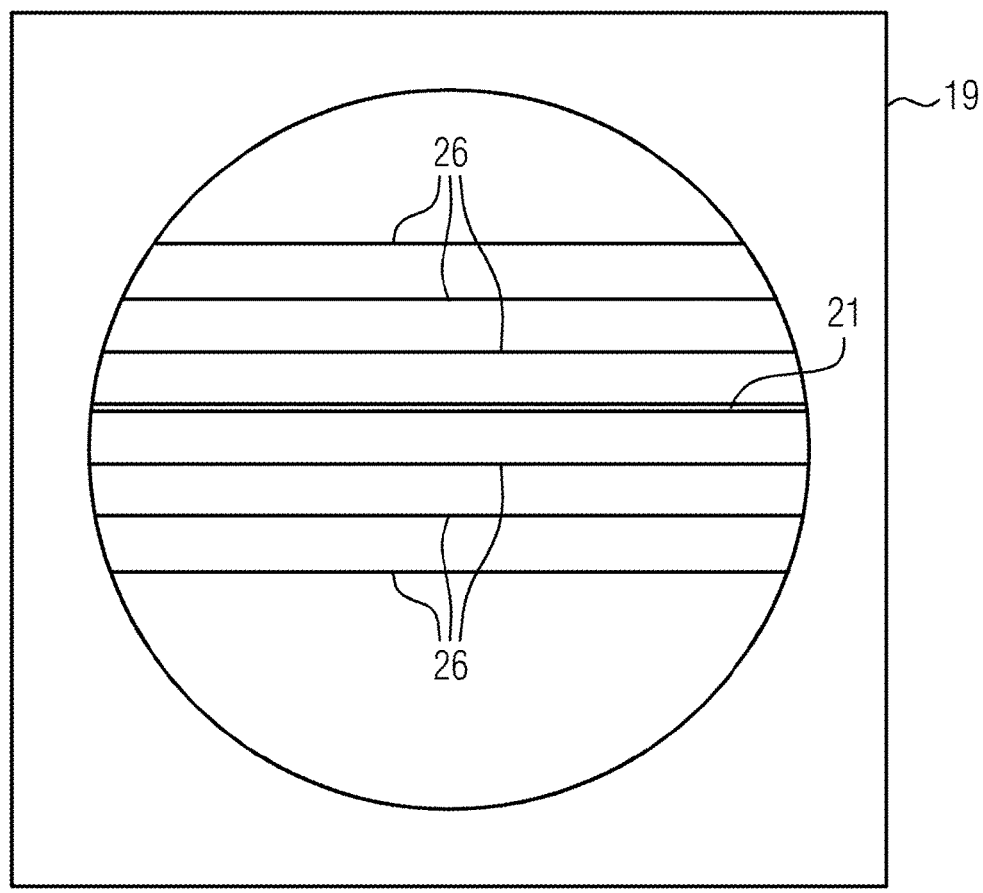
FIG. 3 shows the display of an indication element on a display screen.

For the purposes of aligning the indication element 21 at an orientation feature or for the purposes of aligning part of a bone 6 at the indication element 21, an x-ray image showing the indication element 21 and the position thereof in relation to the bone 6 is displayed by means of a suitable display instrument, for example a screen 19. In a particularly preferred embodiment of the invention, the position of the indication element 21 is acquired with the aid of a suitable instrument for image processing and display control and subsequently, as depicted in FIG. 3, one or more virtual indication elements 26, preferably in the form of straight lines or the like, are displayed in addition to the real indication element 21, with these virtual indication elements 26 extending parallel to the real indication element 21. In the example depicted in FIG. 3, all indication elements 21, 26 have the same distance from one another. Compared to the variant with only a single rod-shaped or pin-shaped indication element 21, the parallelism of indication element and orientation feature or bone can be determined more easily and more quickly with the aid of the virtual indication elements 26.

As an alternative to calculating and imaging virtual indication elements 26, a real indication element 21 having a plurality of indication element structures arranged parallel to one another is used in a further embodiment of the invention. Since this relates to real physical structures, they are depicted on the screen, and so imaging of virtual indication elements 26 is not required for the quicker determination of the parallelism. By way of example, an indication element 21 embodied in the style of a comb or a rake can be used herefor.

The above-described method for determining the antetorsion angle 5 can be used for the healthy and the repositioned side.

Preferably, the control unit 18 or a different suitable evaluation unit is embodied to establish the femoral antetorsion angle 5 from the position information established therebefore. Moreover, the control unit 18 can also be embodied for automatic positioning of the indication element 21. Here, this is preferably a data processing unit with functional modules, which are embodied as hardware modules or software modules. Expressed differently, the invention, to the extent that it relates to the data processing unit, can be implemented in the form of computer hardware or in the form of computer software or in a combination of hardware and software. To the extent that the invention is implemented in the form of software, i.e. as a computer program, all described functions are implemented by computer program instructions when the computer program is executed on a computer with a processor. This relates, in particular, to computer program instructions for establishing the femoral antetorsion angle 5 and to computer program instructions for actuating a holder 22 for the automatic change in position of the indication element 21 on the basis of image information with respect to the position of the femoral neck axis 7. The computer program instructions in this case are implemented in a manner known per se in any programming language and can be provided to the computer in any form, for example in the form of data packets that are transmitted over a computer network or in the form of a computer program stored on a disk, a CD-ROM or a different data medium.

If the positioning of the indication element 21 is carried out manually, a screen 19 or a different suitable display instrument is provided for imaging the x-ray image recorded by the C-arm, on the basis of which x-ray image the parallel alignment of the indication element 21 in relation to the femoral neck axis 7 is implemented.

In conjunction with the present invention, it is possible to carry out a novel method for setting or correcting the angle position of bone fragments in relation to one another, as occurs, for example, during an operation following a fracture. Here, the antetorsion angles 5 of both sides are compared in order to check the antetorsion angle of the fractured side and possibly correct it.

This method for setting the torsion angle 5 between two bone fragments 1, 2 twisted relative to one another about the axis 3 of a bone shaft 4 comprises the following steps: a) determining the angle position of the bone fragments in relation to one another, b) comparing the angle position of the bone fragments with a previously determined reference angle position, in particular with an angle position in the case of a healthy bone, c) repositioning the bone fragments taking into account the result of the comparison of the angle positions. Here, steps a) to c) may optionally be repeated a number of times until a desired correspondence of the angle positions is achieved. There can also be initial repositioning prior to the first execution of step a).

Here, determining the angle positions of the bone fragments in relation to one another (step a) and/or determining the reference angle position used in step b) is preferably implemented according to the above-described angle determination method using 2D x-ray images. In other words, in respect of the femoral neck axis 7, the antetorsion angle 5 of the fractured bone is compared to a reference angle of the antetorsion angle 5 in such a way that an indication element 21 is assigned to the bone to be corrected, the position of which after successful repositioning corresponds to the position of the femoral neck axis 7 or the position of the indication element 21 when establishing the reference angle. In respect of the condyle tangent 8, the comparison is once again carried out in relation to a display of the condyles 2, overlapping where possible, in the x-ray image.

Here, the reference angle position need not necessarily be determined during the operation. Instead, the reference value of the torsion angle 5 can already be established prior to the operation. Moreover, the reference angle position need not necessarily be determined using the angle determination method according to the invention. Instead, the reference angle position can also be established using a different method, for example it can also be established using 3D x-ray recordings. What is essential is that the intraoperative determination of the torsion angle 5 in the case of the parts of the fractured bone is implemented using the angle determination method according to the invention.

Even though the invention was illustrated more closely and described in detail by the preferred exemplary embodiment, the invention is not restricted by the disclosed examples and other variations can be derived herefrom by a person skilled in the art, without departing from the scope of protection of the invention.

The following is a summary list of reference numerals and the corresponding structure used in the above description of the invention:
1 Femoral neck
2 Femoral condyles
3 Femoral shaft axis
4 Femoral shaft
5 Femoral antetorsion angle
6 Femur
7 Femoral neck axis
8 Femoral condyle tangent
9 Patient body
11 C-arm
12 X-ray radiation source
13 X-ray radiation receiver
14 Operating table plane, patient plane
15 Operating table
16 Central x-ray beam, central ray
17 Detector plane
18 Control unit
19 Screen
21 Indication element
22 Holder
23 Longitudinal axis of the indication element
24 Angle measuring device of the indication element
25 Angle measuring device of the C-arm
26 Virtual indication element

The invention claimed is:

1. A method of determining an angle between two parts of a bone of a patient that are twisted relative to one another about an axis of a bone shaft of the bone, the method comprising:
    establishing a position of a first orientation feature assigned to a first part of the bone using an x-ray imaging method;
    establishing a position of a second orientation feature assigned to a second part of the bone using the x-ray imaging method;
    providing an indication element being an elongate construction element having a defined longitudinal axis; for establishing the position of at least one of the first and second orientation features, positioning the indication element outside of the patient's body relative to the at least one of the first and second orientation features, wherein the indication element is visible in an x-ray image to be taken, and moving the indication element relative to the bone for positioning the indication element based on a plurality of recordings obtained by the x-ray imaging method; and
    determining the angle between the first and second parts of the bone from the positions of the first and second orientation features.

2. The method according to claim 1, wherein the bone is a femur, the first orientation feature is a femoral neck axis, the second orientation feature is a condyle tangent or a condyle plane, and the determining step comprises determining a femoral antetorsion angle.

3. The method according to claim 1, which comprises recording the plurality of recordings of the bone used for the positioning of the indication element from mutually different recording angles.

4. The method according to claim 1, which comprises recording the recordings of the bone when establishing the position of at least one of the orientation features using the x-ray imaging method and aligning a recording device relative to the relevant orientation feature on the basis of the recordings.

5. The method according to claim 1, wherein the first and second orientation features are bone-inherent orientation features.

6. The method according to claim 1, wherein the imaging method used for establishing at least one of the positions of the first or second orientation features is an x-ray projection method.

7. The method according to claim 1, which comprises carrying out the method steps intraoperatively.

8. The method according to claim 1, which comprises holding the indication element by hand.

9. The method according to claim 1, which comprises holding the indication element by way of a holder fastened to an operating table or way of a stand.

10. A system for determining an angle between two parts of a bone that are twisted relative to one another about an axis of a bone shaft of the bone of a patient, the system comprising:
    a device for establishing a position of a first orientation feature assigned to a first part of the bone, the device including at least one indication element positionable relative to the first orientation feature on the basis of a number of recordings obtained by an x-ray imaging method, the indication element being an elongate construction element having a defined longitudinal axis, and a holder fastened to an operating table or a stand configured to hold said indication element outside of the patient and to move said indication element relative to the bone of the patient;
    a device for establishing a position of a second orientation feature assigned to a second part of the bone; and
    a device for determining the angle between the first and second parts of the bone from the positions of the first and second orientation features.

11. The system according to claim 10, wherein the bone is a femur, the first orientation feature is a femoral neck axis, the second orientation feature is a condyle tangent or a condyle plane, and the angle to be determined is a femoral antetorsion angle.

12. The system according to claim 10, wherein the indication element is configured for alignment with the first orientation feature.

\* \* \* \* \*